US00PP18103P2

(12) United States Plant Patent
Olesen

(10) Patent No.: US PP18,103 P2
(45) Date of Patent: Oct. 2, 2007

(54) MINIATURE ROSE PLANT NAMED 'POULPAH031'

(50) Latin Name: ***Rosa* hybrid**
Varietal Denomination: Poulpah031

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 11/389,464

(22) Filed: Mar. 23, 2006

(51) Int. Cl.
*A01H 5/00* (2006.01)

(52) U.S. Cl. ..... Plt./121

(58) Field of Classification Search ..... Plt./121, Plt./122

See application file for complete search history.

*Primary Examiner*—Kent Bell
*Assistant Examiner*—June Hwu

(57) ABSTRACT

A new miniature rose plant that has abundant, deep pink flowers and attractive foliage. The variety successfully propagates from softwood cuttings and is suitable for year-round production in commercial glasshouses. This new and distinct variety has shown to be uniform and stable in the resulting generations from asexual propagation.

2 Drawing Sheets

Botanical designation: *Rosa* hybrid.
Variety denomination: 'Poulpah031'.

SUMMARY OF THE INVENTION

The present invention constitutes a new and distinct variety of miniature rose plant which originated from a controlled crossing between the female seed parent, an unnamed seedling, and the male pollen parent, an unnamed seedling.

The two parents were crossed during the summer of 2001 and the resulting seeds were planted in a controlled environment in Fredensborg, Denmark. The new variety, named 'Poulpah031', originated as a single seedling from the stated cross.

The new variety may be distinguished from its female seed parent by the following combination of characteristics:

1. The seed parent has smaller flowers than 'Poulpah031'.
2. Flowers of the seed parent are light pink, while flowers of 'Poulpah031' are deep pink.

The new variety may be distinguished from its male pollen parent by the following combination of characteristics:

1. The pollen parent has more flower petals than 'Poulpah031'.
2. The pollen parent is less compact than 'Poulpah031'.

The objective of the hybridization of this rose variety for commercial culture was to create a new and distinct variety with unique qualities, such as:

1. Uniform and abundant deep pink flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpah031' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpah031' was selected by the inventor as a single plant from the progeny of the hybridization in 2001.

Asexual reproduction of 'Poulpah031' by cuttings and traditional budding was first done by Mogens N. Olesen in the nursery in Fredensborg, Denmark in 2002. This initial and other subsequent propagations conducted in controlled environments have demonstrated that the characteristics of 'Poulpah031' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpah031'. Specifically illustrated in the drawings.

DETAILED DESCRIPTION OF THE VARIETY

Figures 1A, 1B, 1C, 1D:
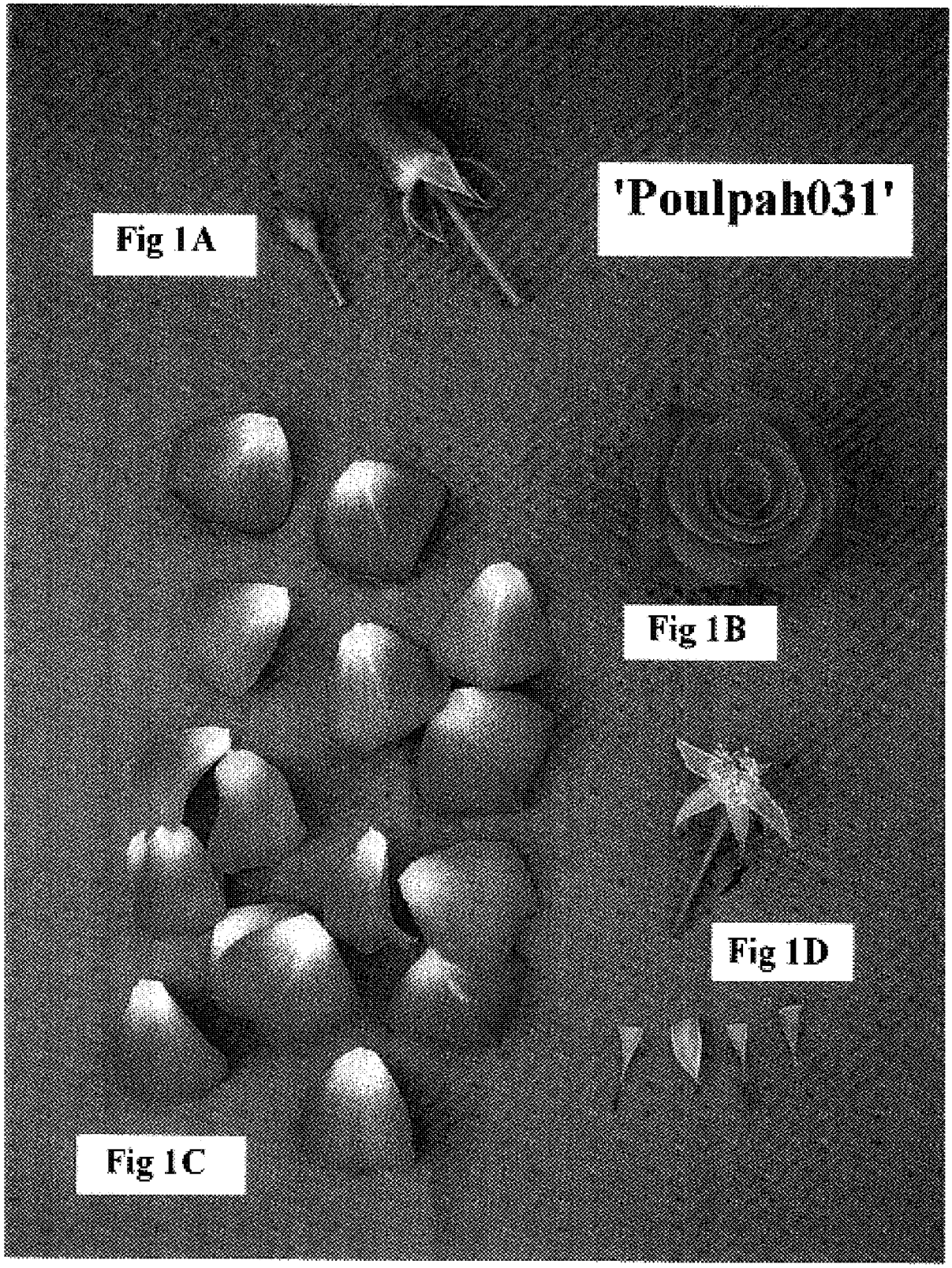
FIG. 1A; Flower bud and partially opened flower.
FIG. 1B; Open flower.
FIG. 1C; Flower petals, detached.
FIG. 1D; Sepals, receptacle, and pedicel.
Figures 2A, 2B, 2C:
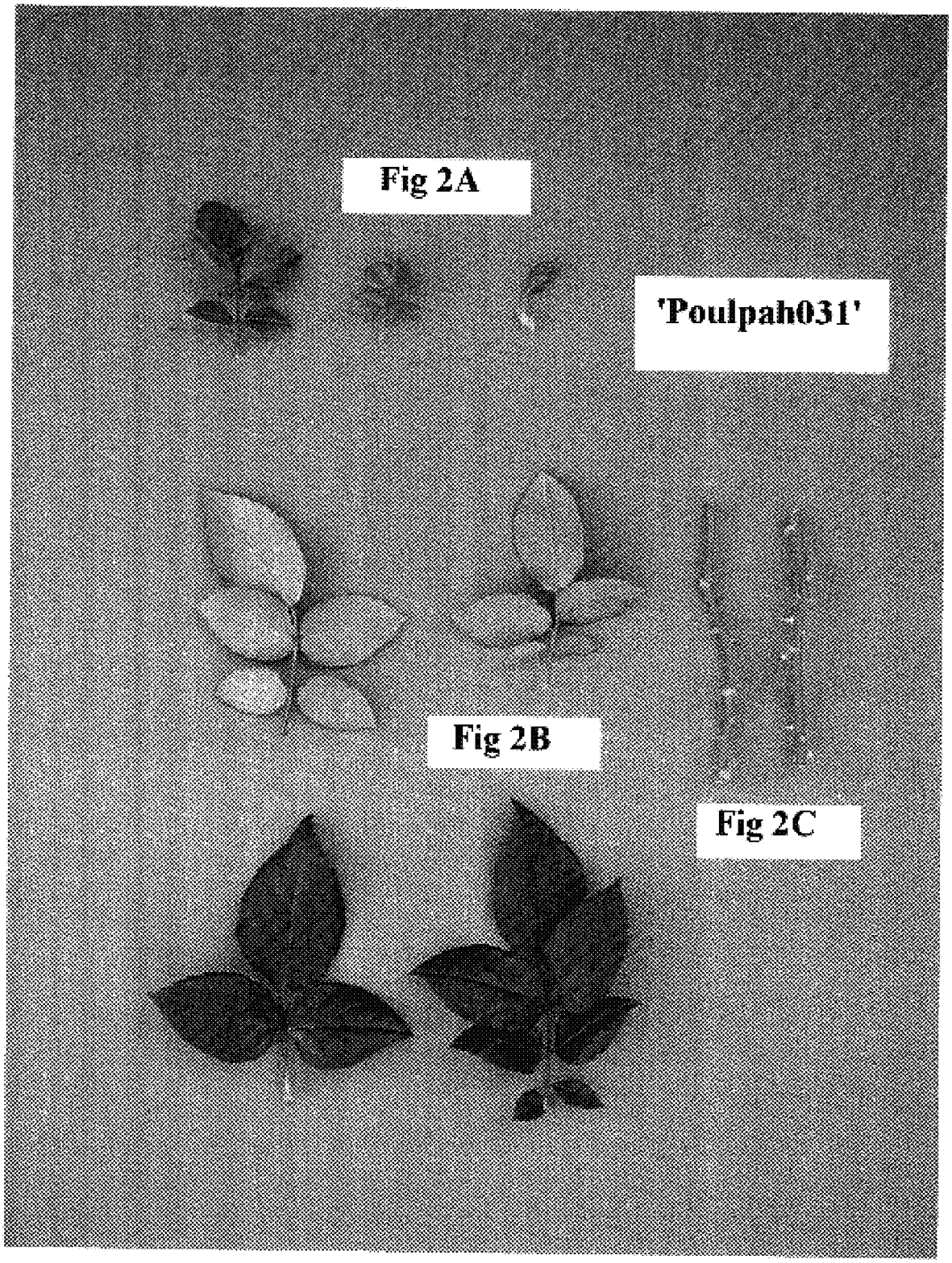
FIG. 2A; Juvenile leaves.
FIG. 2B; Mature leaves, upper and undersurfaces.
FIG. 2C; Bare stem.

The following is a description of 'Poulpah031', as observed in its growth in Fredensborg, Denmark. Observed plants are 4 months of age and were cultivated in 12 cm pots. Color references are made using The Royal Horticultural Society (London, England) Colour Chart, 2003, except where common terms of color are used.

For a comparison, several physical characteristics of the rose variety 'Poulody', U.S. Plant Pat. No. 11,514, are compared to 'Poulpah031' in Chart 1.

CHART 1

| | 'Poulpah031' | 'Poulody' |
|---|---|---|
| Petalage: | 15 to 20 | 50 to 60 |
| Flower Diameter: | 70 to 90 mm | 45 mm |
| Petal color, upper surface: | Red-Purple N 57A | Red-Purple 57B-57C |

FLOWER AND FLOWER BUD

Blooming habit: Continuous.

Flower bud:

*Size.*—Upon opening, 30 mm in length from base of receptacle to end of bud. 11 mm diameter average.

*Bud form.*—Urceolate to ovate.

*Bud color.*—As sepals unfold, petals underneath are Red-Purple Group N57A.

*Sepals.*—Upper Surface: Color: Yellow-Green Group 146D. Texture: Strongly Pubescent. Lower Surface: Color: Yellow-Green Group 146A to 146B. Texture: Smooth. Shape: Apex: Cirrhose. Base: Flat at union with receptacle. Margins: Margins have weak foliaceous appendages on three of the five sepals. Stipitate glands are abundant to medium. Size: Normally 32 mm long by 9 mm wide.

*Receptacle.*—Surface Texture: Smooth. Shape: Urn-shaped. Size: 8 mm (h)×10 mm (w). Color: Yellow-Green Group 144A. Anthocyanin: None observed.

*Pedicel.*—Surface: Somewhat rough with stipitate glands. Length: 40 to 45 mm average length. Diameter: Normally 3 mm. Color: Yellow-Green Group 144A to 144B. Strength: Strong.

*Borne.*—Singularly.

Flower bloom:

*Fragrance.*—Light to moderate floral scent.

*Duration.*—As a pot plant, flowers last from 21 to 28 days. Petals fall cleanly away from plant after flowers have matured.

*Size.*—Open flower diameter is normally 70 to 90 mm. Average flower depth is 35 mm.

*Form.*—Generally flowers have a high-pointed center which is tightly closed.

*Shape of flower, side view.*—Upon opening, the upper portion is flat. The lower portion is flat. After opening, the upper portion is convex. The lower portion is flat to flattened concave.

*Petalage.*—There are normally 15 to 20 petals, 3 to 5 of which are petaloids.

Color:

*Upon opening, petals.*—Outermost petals: Upper Surface: Red-Purple Group N57A with streaks of Red-Purple Group 62B. Lower Surface: Red-Purple Group N57A with streaks of Red-Purple Group 62B to Greyed-White Group 157A. Innermost petals: Upper Surface: Red-Purple Group N57A with streaks of Red-Purple Group 62B. Lower Surface: Red-Purple Group N57A with streaks of Red-Purple Group 62B to Greyed-White Group 157A.

*Upon opening, basal petal spots.*—Upper Surface: Yellow Group 2D. Lower Surface: Yellow Group 2D.

*After opening, petals.*—Outermost petals: Upper Surface: Red-Purple Group N57A with streaks of Red-Purple Group 62B. Lower Surface: Red-Purple Group N57A with streaks of Red-Purple Group 62B to Greyed-White Group 157A. Innermost petals: Upper Surface: Red-Purple Group N57A with streaks of Red-Purple Group 62B. Lower Surface: Red-Purple Group N57A with streaks of Red-Purple Group 62B to Greyed-White Group 157A.

*After opening, basal petal spots.*—Upper Surface: Yellow Group 2D to Yellow-Orange Group 18C. Lower Surface: Yellow Group 2D.

General tonality: Opened flowers are Red-Purple Group N57A. After flowers have fully matured, general tonality changes to Red-Purple Group N57A with intonations of Red-Purple Group 68C.

Petals:

*Petal reflex.*—Slightly reflexed.

*Petal margin.*—Entire.

*Shape.*—Broad elliptical. Base: Rounded. Apex: Acute and obtuse.

*Size.*—Petal size varies. Outer petals: 52 mm (l)×45 mm (w). Inner petals: 37 mm (l)×35 mm (w).

*Texture.*—Smooth.

*Thickness.*—Above average.

Petaloids:

*Quantity.*—Normally 3 to 5.

*Size.*—12 mm long; 5 mm wide.

*Shape.*—Irregular.

*Color.*—Red-Purple Group N57A with Streaks of Yellow Group 2D to Yellow-Orange Group 18C.

Reproductive organs:

*Pollen.*—None observed.

*Anthers.*—Size: Normally 3.5 mm long. Color: Yellow Group 12C. Quantity: 100 to 110.

*Filaments.*—Color: Yellow-Orange Group 22C. Length: Normally 10 mm.

*Pistils.*—Length: 4 mm long. Quantity: 50 to 55.

*Stigmas.*—Slightly inferior relative to the length of the filaments and the height of the anthers. Color: Greyed-Yellow Group 160B.

*Styles.*—Color: Red Group 53C.

*Seed formation.*—Not observed.

PLANT

Plant growth: Compact, upright, and bushy. When grown as a 12 cm pot plant on its own roots, the average height of the plant itself is 27 cm and the average width is 20 cm.

Stems:

*Color.*—Young wood: Yellow-Green Group 146B. Older wood: Yellow-Green Group 146A.

*Internodal distance.*—On mature canes, average distance between nodes is 20 mm.

*Length of stems.*—On average, canes are 15 to 18 cm from the base of the stem to the flowering portion.

*Surface texture.*—Young wood: Smooth. Older wood: Somewhat rough with small prickles.

Prickles:

*Incidence.*—10 to 12 mm per 10 cm of stem.

*Size.*—Average length is 5 mm.

*Color.*—Juvenile prickles are Greyed-Yellow Group 162D with Orange-Red Group 35C. Mature prickles are Greyed-Yellow Group 162D.

Plant foliage: Normal number of leaflets on normal leaves in middle of the stem: 5 to 7 leaflets.

*Compound leaf size.*—85 to 105 mm (l)×60 to 80 mm (w).

*Quantity.*—5 leaves per 10 cm of stem.

*Color.*—

*Juvenile foliage.*—Upper Leaf Surface: Yellow-Green Group 146A. Lower Leaf Surface: Yellow-Green Group 147B. The undersides occasionally have anthocyanic intonations the color of Greyed-Purple Group 184B. Mature foliage: Upper Leaf Surface: Yellow-Green Group 147A. Lower Leaf Surface: Yellow-Green Group 191A, with occasional intonations of Greyed-Purple Group 184B.

Plant leaves and leaflets:

*Stipules.*—Size: 8 to 10 mm. Shape: Linear, slightly broad based with outward extending apecies. Margins: Finely serrated with many stipitate glands. Color: Yellow-Green Group 146A to 147A.

*Petiole.*—Length: Normally 15 mm. Diameter: 2 mm on average. Upper surface: Color: Green Group 138A. Anthocyanin: Greyed-Purple Group 183A. Underneath: Numerous stipitate glands observed. Lower surface: Color: Yellow-Green Group 146D. Observations: Small numerous prickles and stipitate glands observed.

*Rachis.*—Size: 35 mm average. Upper Surface: Color: Green Group 138A to Yellow-Green Group 144A with anthocyanic pigments Greyed-Purple Group 183A. Observations: Numerous stipitate glands. Lower Surface Color: Yellow-Green Group 146D. Observations: Numerous small prickles observed.

*Leaflet.*—Size: 50 to 55 mm in length by 27 to 30 mm wide. Edge: Serrated. General Shape: Ovate. Apex Shape: Acute. Base Shape: Obtuse to rounded. Texture: Smooth. Thickness: Average. Arrangement: Odd pinnate. Venation: Reticulate. Leaf Gloss: Very glossy finish.

Disease resistance: Average resistance to powdery and downy mildew, black spot, and *Botrytis* under normal growing conditions in Fredensborg, Denmark.

It is claimed:

1. A new and distinct variety of rose plant of the miniature class named 'Poulpah031', substantially as illustrated and described herein, due to its abundant, deep pink flowers, vigorous growth, compact habit, substantially for production from softwood cuttings in pots, and durable flowers and foliage that make the variety suitable for distribution in the floral industry.

* * * * *

'Poulpah031'

'Poulpah031'